(12) United States Patent
Filutowski

(10) Patent No.: US 12,023,206 B2
(45) Date of Patent: Jul. 2, 2024

(54) WEARABLE FOOT CONTROLLER FOR SURGICAL EQUIPMENT AND RELATED METHODS

(71) Applicant: Oliver Filutowski, Tampa, FL (US)

(72) Inventor: Oliver Filutowski, Tampa, FL (US)

(73) Assignee: ORASI LLC, Longwood, FL (US)

( * ) Notice: Subject to any disclaimer, the term of this patent is extended or adjusted under 35 U.S.C. 154(b) by 0 days.

(21) Appl. No.: 18/160,470

(22) Filed: Jan. 27, 2023

(65) Prior Publication Data

US 2023/0263589 A1 Aug. 24, 2023

Related U.S. Application Data

(60) Provisional application No. 63/268,323, filed on Feb. 22, 2022.

(51) Int. Cl.
*A61B 90/20* (2016.01)
*A61B 17/00* (2006.01)

(52) U.S. Cl.
CPC .... *A61B 90/20* (2016.02); *A61B 2017/00973* (2013.01)

(58) Field of Classification Search
CPC ................ A61B 90/20; A61B 2017/00973
USPC ............................................................ 606/1
See application file for complete search history.

(56) References Cited

U.S. PATENT DOCUMENTS

| 6,452,120 B1 | 9/2002 | Chen |
| 2009/0293319 A1 | 12/2009 | Anvi |
| 2011/0199393 A1 | 8/2011 | Nurse et al. |
| 2017/0336870 A1 | 11/2017 | Everett et al. |
| 2018/0325207 A1* | 11/2018 | Krasnow ................. A43B 3/38 |
| 2018/0360157 A1* | 12/2018 | Jeong .................. A61B 5/7203 |
| 2019/0302901 A1 | 10/2019 | Tian |

FOREIGN PATENT DOCUMENTS

| DE | 102016210329 | 12/2017 |
| EP | 3744286 | 12/2020 |
| WO | WO2007051628 | 5/2007 |
| WO | WO2019232002 | 12/2019 |

* cited by examiner

*Primary Examiner* — Aaron F Roane
(74) *Attorney, Agent, or Firm* — Allen, Dyer, Doppelt + Gilchrist, PA

(57) ABSTRACT

A wearable foot controller for a surgical instrument may include a body configured to be worn on a foot and including a heel portion and a ball portion on an opposite end of the body from the heel portion, a heel pressure sensor, a ball pressure sensor, a heel movement sensor, a ball movement sensor, and a processor. The processor may be configured to detect activation of the heel pressure sensor and generate control data for the surgical instrument based upon the ball movement sensor when the heel pressure sensor is activated using the processor, and detect activation of the ball pressure sensor and generate control data for the surgical instrument based upon the heel movement sensor when the ball pressure sensor is activated using the processor. The processor may also be configured to communicate the control data from the processor to the surgical instrument via a communications link.

15 Claims, 8 Drawing Sheets

WEARABLE FOOT CONTROLLER FOR SURGICAL EQUIPMENT AND RELATED METHODS

CROSS-REFERENCE TO RELATED APPLICATIONS

This application claims the benefit of U.S. app. Ser. No. 63/268,323 filed Feb. 22, 2022, which is hereby incorporated herein in its entirety by reference.

TECHNICAL FIELD

The present disclosure generally relates to surgical equipment, and more particularly to controllers for surgical equipment such as microscopes and related methods.

BACKGROUND

In certain surgical applications, viewing aids are important to help surgeons see fine details and perform precise maneuvers. One such application is in eye surgeries, where a microscope is used to give the surgeon the ability to see acutely and perform delicate steps in the surgical process. Typically, the microscope is controlled by a large, mechanical foot pedal, allowing the surgeon to use his or her hands to operate surgical devices or tools. However, such foot pedals may be somewhat difficult to use. Moreover, they are typically heavy and difficult to move while cleaning the surgery room and reposition for a subsequent surgery.

European Pat. Pub. EP3744286A1 is directed to a microscope system that includes a surgical microscope, an operating device configured to be operated by a user, and a processor configured to receive a command signal from the operating device in response to the user operation and to control the surgical microscope based on the command signal. The operating device comprises a sensor unit configured to detect the user operation and to generate the command signal based on the detected user operation, and the sensor unit is further configured to be worn by the user.

Despite the existence of such systems, further developments in surgical equipment controllers may be desirable in certain applications.

SUMMARY

A wearable foot controller for a surgical instrument may include a body configured to be worn on a foot and including a heel portion and a ball portion on an opposite end of the body from the heel portion, a heel pressure sensor coupled to the heel portion of the body, a ball pressure sensor coupled to the ball portion of the body, a heel movement sensor coupled to the heel portion of the body, a ball movement sensor coupled to the ball portion of the body, and a processor coupled to the body. The processor may be configured to detect activation of the heel pressure sensor and generate control data for the surgical instrument based upon the ball movement sensor when the heel pressure sensor is activated, and detect activation of the ball pressure sensor and generate control data for the surgical instrument based upon the heel movement sensor when the ball pressure sensor is activated. The processor may also be configured to communicate the control data from the processor to the surgical instrument via a communications link.

In an example embodiment, the processor may be further configured to activate the ball movement sensor responsive to activation of the heel pressure sensor, and activate the heel movement sensor responsive to activation of the ball pressure sensor. In accordance with another example embodiment, the processor may be configured to activate the ball movement sensor responsive to deactivation of the ball pressure sensor, and activate the heel movement sensor responsive to deactivation of the heel pressure sensor.

In one example implementation, the surgical instrument may be a microscope, and the control data may relate to at least one of pan, tilt, zoom, illumination and focus of the microscope. In some embodiments, the control data may relate to image recording using the microscope.

In some embodiments, the processor may be operable in a learning mode to associate at least one movement detected from at least one of the heel and ball movement sensors with a given control command. In some configurations, the processor may be further configured to change a weight associated with the control data based upon an adjustable sensitivity ratio. In an example implementation, the processor may be operable in an instructor mode in which the determined control commands override control commands from another surgical instrument controller.

In some configurations, the processor may be further configured to detect a series of movements from at least one of the heel and ball movement sensors, and switch between active and inactive states responsive to the series of movements. By way of example, the communications link may comprise a wireless communications link.

A related method for controlling a surgical instrument using a wearable foot controller, such as the one described briefly above, is also provided. The method may include detecting activation of the heel pressure sensor and generating control data for the surgical instrument based upon the ball movement sensor when the heel pressure sensor is activated, and detecting activation of the ball pressure sensor and generating control data for the surgical instrument based upon the heel movement sensor when the ball pressure sensor is activated. The method may further include communicating the control data from the wearable foot controller to the surgical instrument via a communications link.

A related non-transitory computer-readable medium for a wearable foot controller, such as the one described briefly above, is also provided. The non-transitory medium may have computer-executable instructions for causing the processor of the wearable foot controller to perform steps including detecting activation of the heel pressure sensor and generating control data for the surgical instrument based upon the ball movement sensor when the heel pressure sensor is activated, and detecting activation of the ball pressure sensor and generating control data for the surgical instrument based upon the heel movement sensor when the ball pressure sensor is activated. The steps may further include communicating the control data to the surgical instrument via a communications link.

DETAILED DESCRIPTION

The present description is made with reference to various example embodiments. However, many different embodiments may be used, and thus, the description should not be construed as limited to the embodiments set forth herein. Rather, these embodiments are provided so that this disclosure will be thorough and complete. Like numbers refer to like elements or steps throughout.

Figure 1:
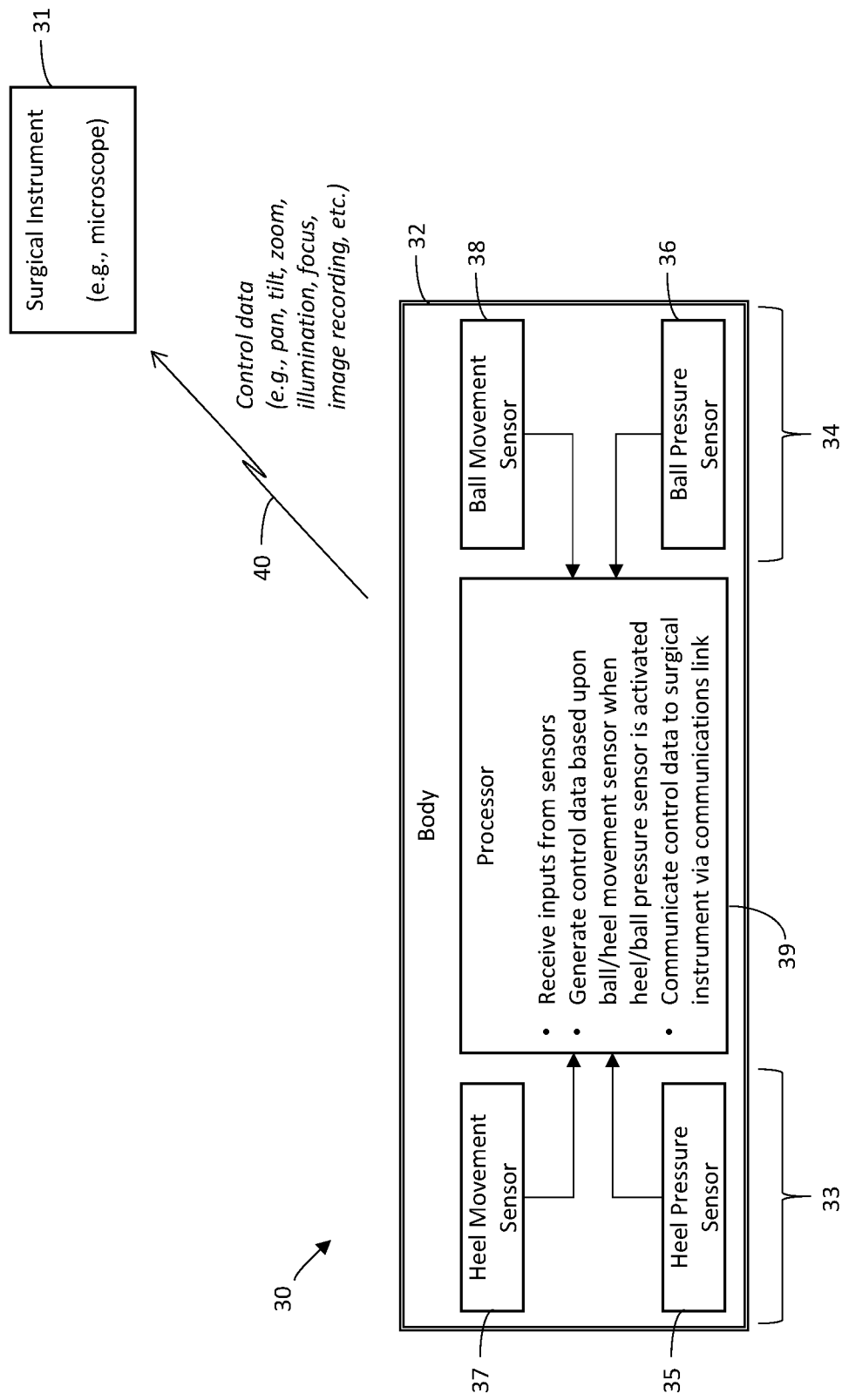
FIG. 1 is a schematic block diagram of a wearable foot controller for surgical instruments in accordance with an example embodiment.

Referring initially to FIG. 1, a wearable foot controller or device 30 for controlling a medical instrument 31, such as a microscope for surgical eye procedures (e.g., laser eye surgeries, etc.), is first described. The wearable foot controller 30 illustratively includes a body 32 configured to be worn on a foot of a user and including a heel portion 33 and a ball portion 34 on an opposite end of the body 32 from the heel portion. A heel pressure sensor 35 is coupled to the heel portion 33 of the body 32, a ball pressure sensor 36 is coupled to the ball portion 34 of the body, a heel movement sensor 37 is coupled to the heel portion of the body, and a ball movement sensor 38 is coupled to the ball portion of the body. The wearable foot controller 30 further illustratively includes a processor 39 coupled to the body 32. The processor 39 may be implemented using suitable hardware (e.g., microprocessor, etc.) and non-transitory computer-readable medium having computer-implemented instructions for causing the hardware to perform the various operations discussed herein. The sensors 35-38 and processor 39 may be wholly or partially embedded within the body 32 or attached to a surface thereof in different embodiments.

More particularly, the processor 39 is configured to detect activation of the heel pressure sensor 35 and generate control data for the surgical instrument 31 based upon the ball movement sensor 38 when the heel pressure sensor is activated. Furthermore, the processor 39 also detects activation of the ball pressure sensor 36 and generates control data for the surgical instrument 31 based upon the heel movement sensor 37 when the ball pressure sensor is activated. Furthermore, the processor 39 is also configured to communicate the control data to the surgical instrument 31 via a communications link 40. In an example implementation, the communications link may be wireless (e.g., Wi-Fi, ultrawide band (UWB), Bluetooth®, etc.), although a wired connection to the surgical instrument 31 may be used in some embodiments.

In this regard, the processor 39 may further include (or have associated therewith) a transmitter or transceiver (e.g., Wi-Fi, UWB, Bluetooth®, etc.) to communicate measurements from one or more of the sensors 35-38 to the controller for the surgical instrument 31. Based upon this output, a controller at the surgical instrument 31 may control various operating parameters or functions. That is, the control data sent by the processor 39 may take the form of measurements, which the surgical instrument 31 controller interprets as different commands for functions to be performed by the surgical instrument. In other embodiments, the processor 39 may interpret the measurements from the sensors and supply the associated commands to the controller of the surgical instrument 31. In the case of a surgical microscope, these functions may include both the movement and the focus of the microscope, pan, tilt, zoom, illumination and in some cases image (video) recording using the microscope. For wireless implementations, a battery(ies) may also be carried by the body 32 for powering the processor 39 and sensor 35-38, and for wired implementations power may be supplied by batteries and/or the wired connection to the surgical instrument 31. Other example surgical instruments which may be controlled by the wearable foot controller 30 include phacoemulsification devices, cautery devices, vitrectomy devices, and indirect laser ophthalmoscopy (these devices are handheld and used by the surgeon, but each has a foot controller for utilization of these technologies). Being able to further adjust their settings and augment their power configurations with a foot controller (rather than requiring a human technician to press the buttons) may be advantageous in various implementations.

Figure 2:
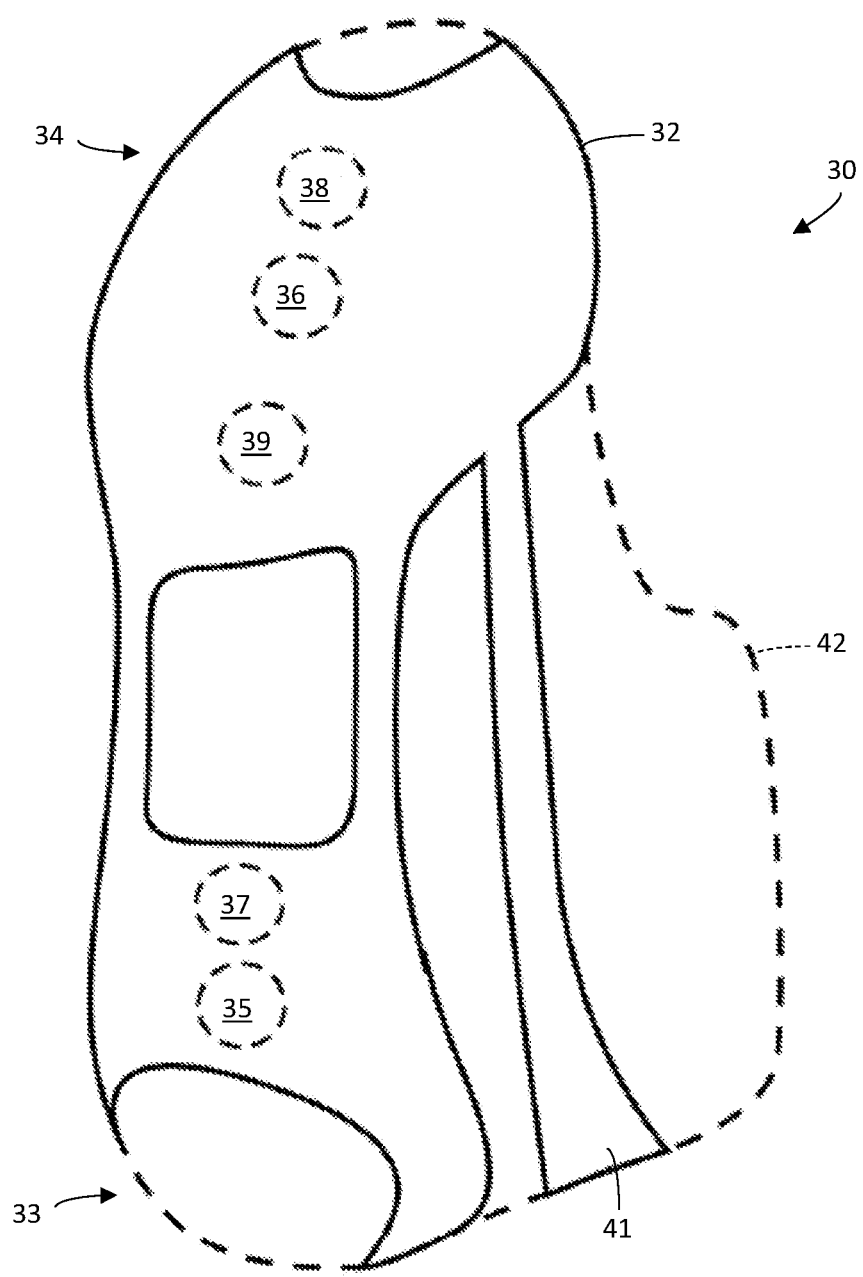
FIG. 2 is a perspective view of the bottom of an example implementation of the wearable foot controller of FIG. 1.
Figure 3:
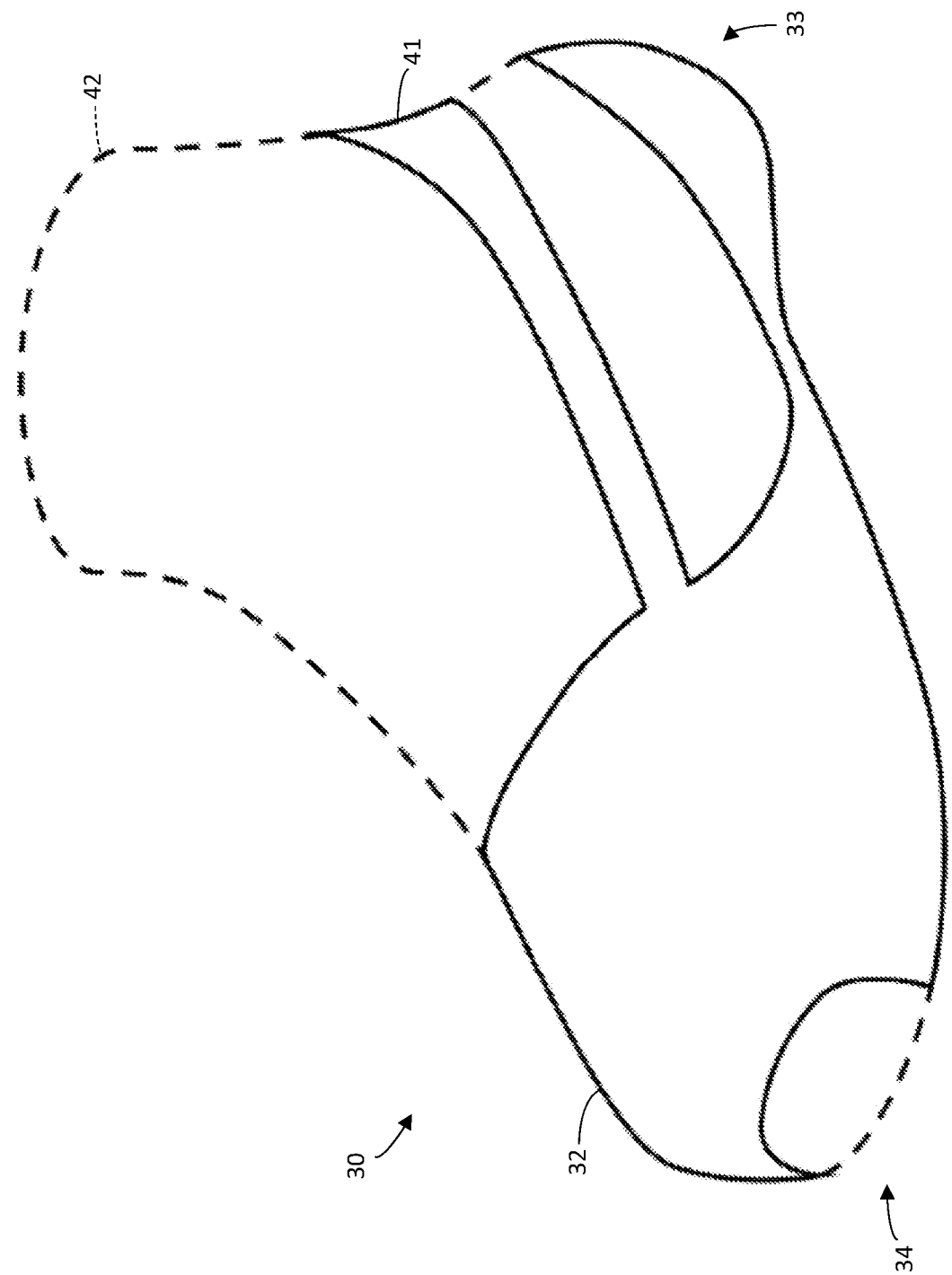
FIG. 3 is a perspective front view of the wearable foot controller of FIG. 2.
Figure 4:
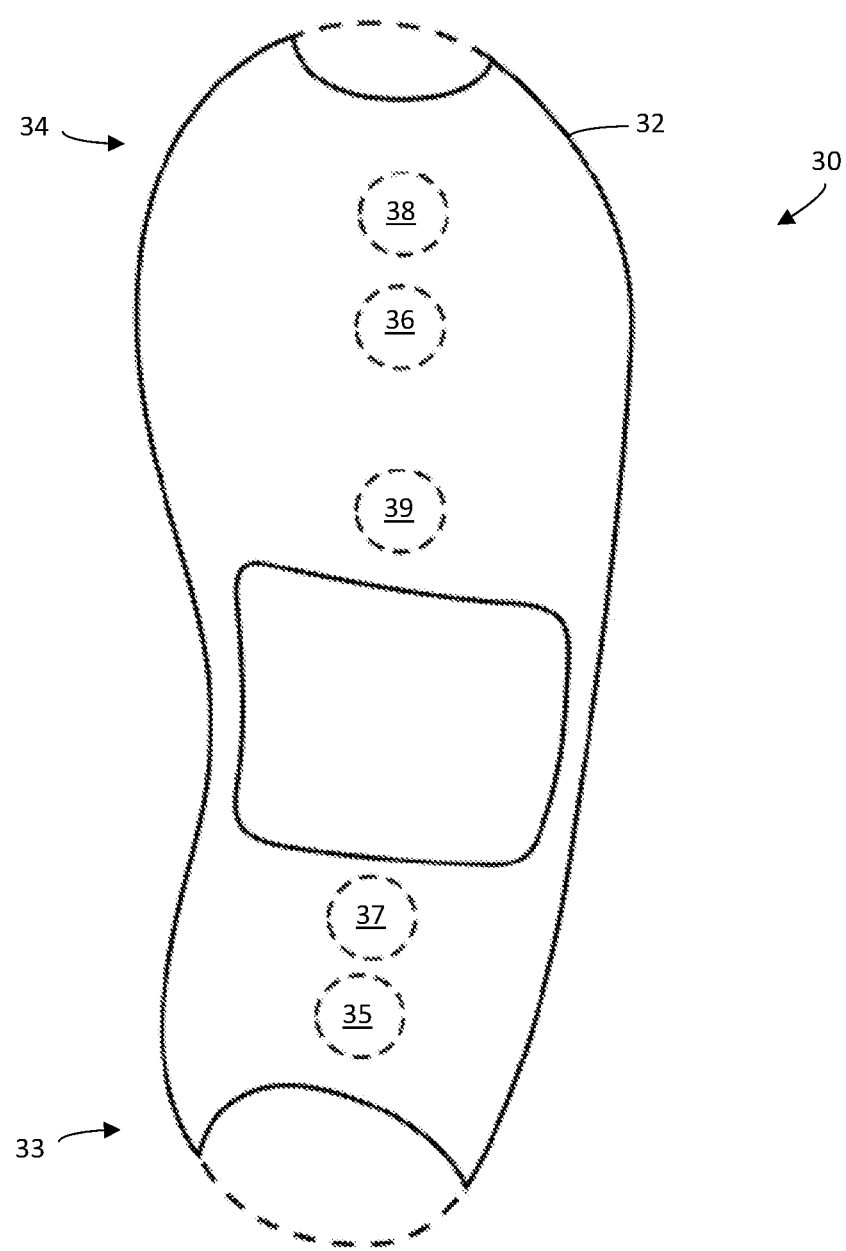
FIG. 4 is a bottom view of the wearable foot controller of FIG. 2.

Referring additionally to FIGS. 2-4, in an example implementation the body 32 takes the form factor of a crampon with a heel strap 41 to fit over a shoe 42. In other embodiments, the body 42 may take the form of a sleeve/sock that fits on the user's foot, or it may have a form factor that resembles a sandal that can similarly fit on the foot or over the user's shoe. In other words, the body 42 may generally take the form of a relatively lightweight surgical foot controller that may be attached to or worn on the user's foot or over a shoe.

By way of example, the movement or motion sensors 37, 38 may include one or more of accelerometers, gyroscopes, etc., and the pressure sensors 35, 36 may take the form of pressure sensitive switches/touch pads. For example, touch pad pressure sensors 35, 36 may be located on the bottom of the body 32 (see FIGS. 2 and 4) to detect when a portion of the body is pressed against the floor. In the illustrated example where respective movement sensors 37, 38 and touch pad pressure sensors 35, 36 are associated with the heel and the ball/toe of the user's foot, detection of whether the user has the heel and/or ball of his or her foot on the ground, and whether the heel and/or ball is being moved, can be determined to provide enhanced control capabilities, as will be discussed further below.

By way of example, the following is a list of how foot movements detected by the motion sensors 37, 38 and touch pad pressure sensors 35, 36 may correlate with corresponding adjustments of a microscope:

- Slide foot forward/backward/right/left→move scope forward/backward/right/left like joystick
- Lift heel and tilt on ball of foot left and right→focus in and out
- Lift ball of foot and tilt on heel of foot left and right-→zoom in and out
- Sweep ball of foot left and right (while keeping heel fixed)→turn brightness up/down
- Double tap whole foot→on/off
- Double tap ball of foot→re-center microscope
- Double tap heel of foot→scroll through lighting settings
- Movement for moving in and out of quiescent and active modes (e.g., a "double tap whole foot" while "triple tap whole foot" would be on/off)

In some embodiments, activation of the pressure sensor 36 at the ball of the foot may activate the corresponding sensor(s) 37 (e.g., accelerometer/gyroscopes) on the heel and suppresses (or deactivates) the sensor(s) 38 at the toe, and vice-versa. That is, to avoid potential interference or contradictory input from the heel and toe sensors, the processor 39 may utilize input from one of the touch/pressure sensors 35, 36 as a trigger to block or ignore input from sensors 37, 38 on the same end of the wearable foot controller 30.

In some example implementations, such as in training institutions, a plurality of wearable foot controllers 30 may be used with the surgical instrument 31. For example, an "attending physician" wearable foot controller 30 may be used, in addition to a wearable foot controller for residents, for training of the residents. In this way, a supervisor may take over control of the surgical instrument 31 (e.g., microscope) during a training session, such as to reorient the trainee's microscope if the trainee gets into trouble. For such an application, the system would allow one of the wearable foot controllers 30 to be designated as the trainee device, and the other as the instructor device such that it is given priority over the trainee device when it provides input to the microscope. Both wearable foot controllers 30 would include their own respective sensors 35-38 and processor 39, as discussed further above, and a controller at the microscope will interface with both and assign priority to the movements from the instructor wearable when appropriate. In some embodiments, the surgical instrument 31 controller may be integrated in the surgical instrument, and in other embodiments it may be a separate controller that connects to an input(s) of the surgical instrument and is configured to interface with the wearable foot controller 30, as noted above.

In accordance with another example aspect, a foot gesture may be used to change the wearable foot controller 30 from a quiescent state (in which foot movements do not result in surgical instrument 31 responses) to an active state (in which foot movements cause corresponding surgical instrument responses). For example, the foot gesture may be to briefly lift one's foot and place it back down. Once activated, the wearable foot controller 30 may remain in an active state until the same gesture is repeated or a separate gesture is performed, returning it to the quiescent state. This would enable the user to choose when the surgical instrument 31 would respond to foot movements and when it would not.

Use of the above-described wearable foot controller 30 to control operation of the surgical instrument 31 may provide several benefits. For example, these may include:
Improved dexterity;
Proper fit for the user (e.g., someone with a small foot using a large traditional foot pedal can struggle compared to someone with a large foot);
More space beneath the head of the patient's bed where the legs of the surgeon(s) are positioned for operating (this area is congested with multiple surgeons and their limbs and difficult to access for taller surgeons whose knees strike the bed due to the large height of traditional foot pedals);
Enhanced portability;
Less likely to get in the way while cleaning and preparing the operating room between patients; and
The ability to detect and assign new movement combinations for enhanced control capabilities.

Figure 5:
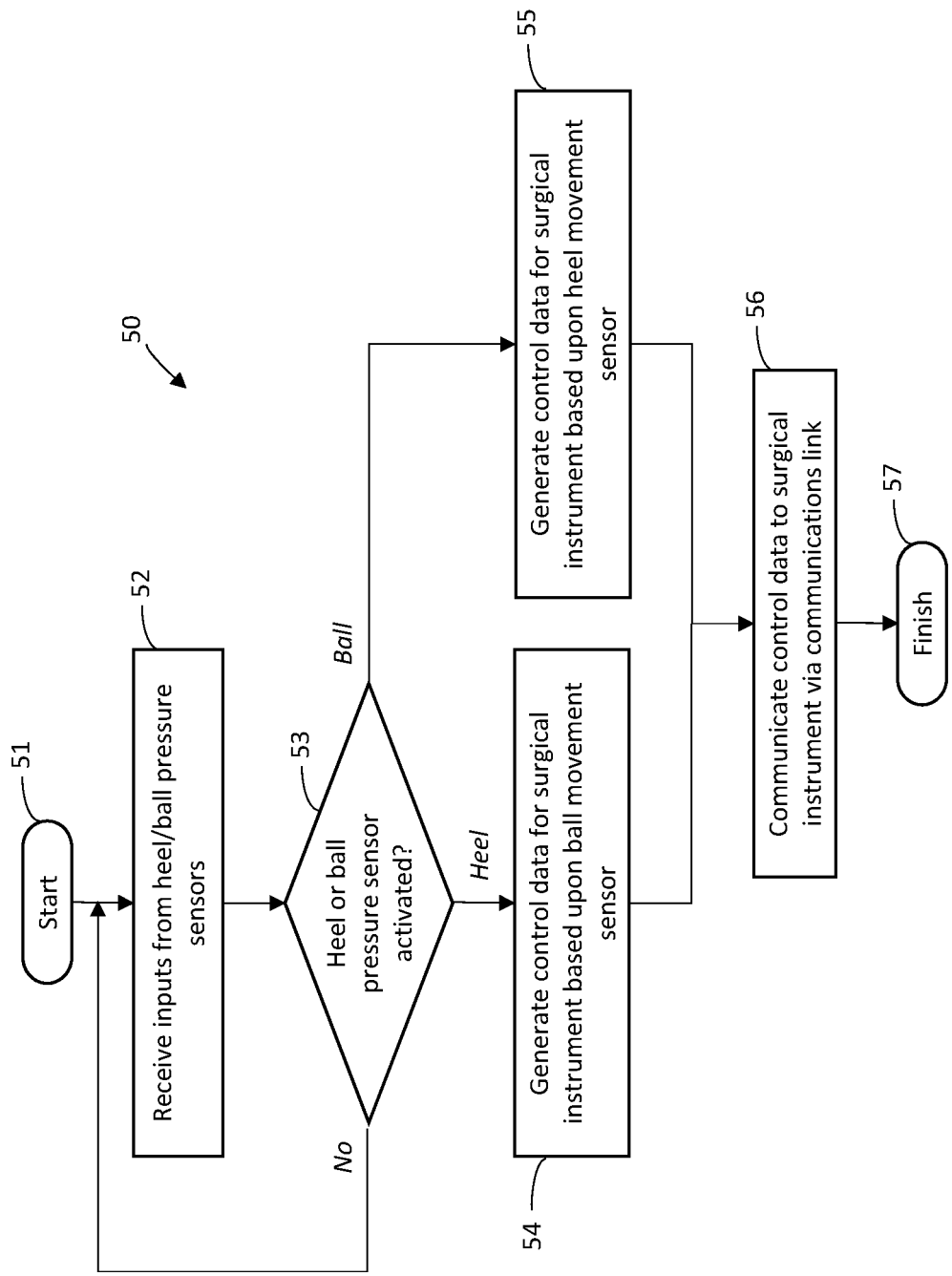
FIGS. 5-7 are flow diagrams illustrating method steps which may be performed by the wearable foot controller of FIG. 1.

Method aspects associated with controlling the surgical instrument 31 using the wearable foot controller 30 are now further described with reference to the flow diagrams 50, 60, 70 of FIGS. 5-7, respectively. Beginning at Block 51, the processor 39 receives input from the heel and ball pressure sensors 35, 36 (Block 52). Upon detection of activation of the heel pressure sensor 35 (Block 53), the processor 39 generates control data for the surgical instrument 31 based upon the ball movement sensor 38, at Block 54. For example, left/right movement detected by the ball movement sensor 38 may result in pan left/right control commands being sent to the surgical instrument 31 (or left/right measurements in embodiments where the surgical instrument 31 interprets the measurements and generates the pan commands). Similarly, when the processor 39 detects activation of the ball pressure sensor 36 (Block 53), it generates control data for the surgical instrument 31 based upon the heel movement sensor 37, at Block 55. For example, left/right movement detected by the heel movement sensor 37 may result in "focus out" and "focus in" control commands being sent to the surgical instrument 31 (or left/right measurements in embodiments where the surgical instrument 31 interprets the measurements and generates the focus commands). The processor 39 communicates the control data signals to the surgical instrument 31 via the communications link 40, as noted above, which may be done in real or near-real time, at Block 56. The method of FIG. 5 illustratively concludes at Block 57.

Figure 6A:
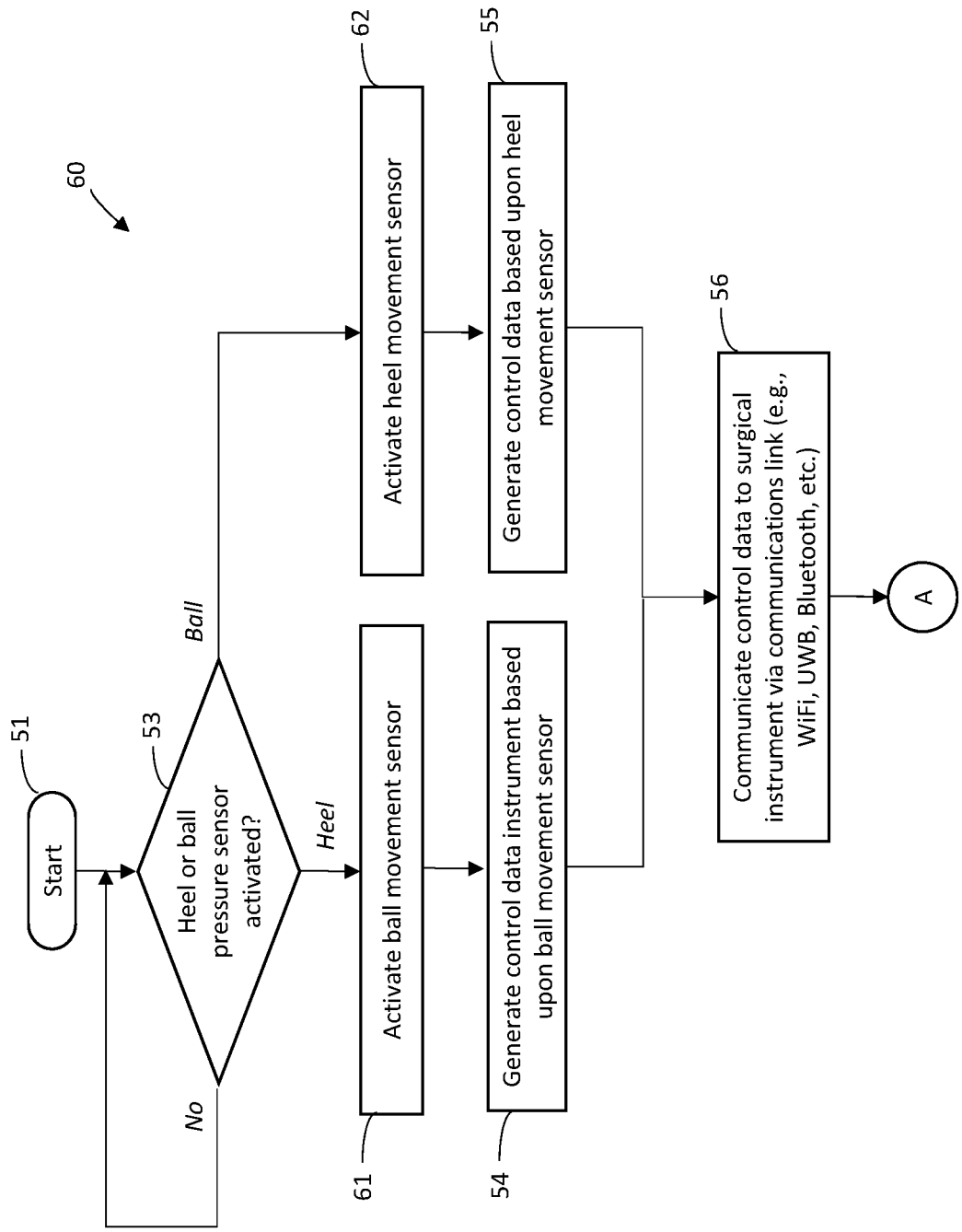
Figure 6B:
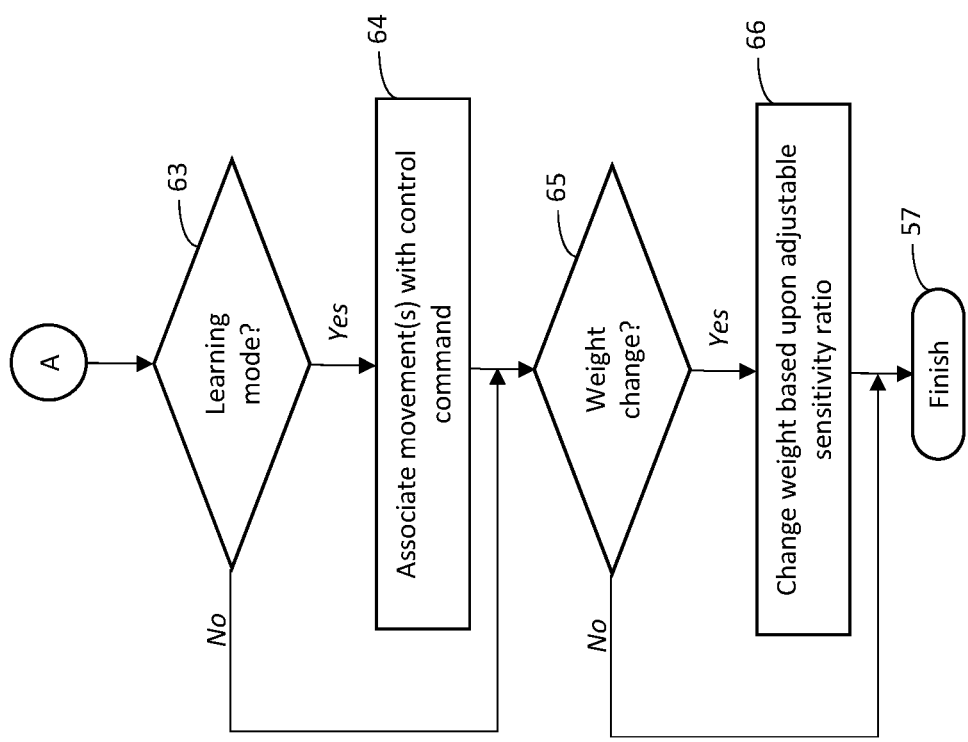
Figure 7:
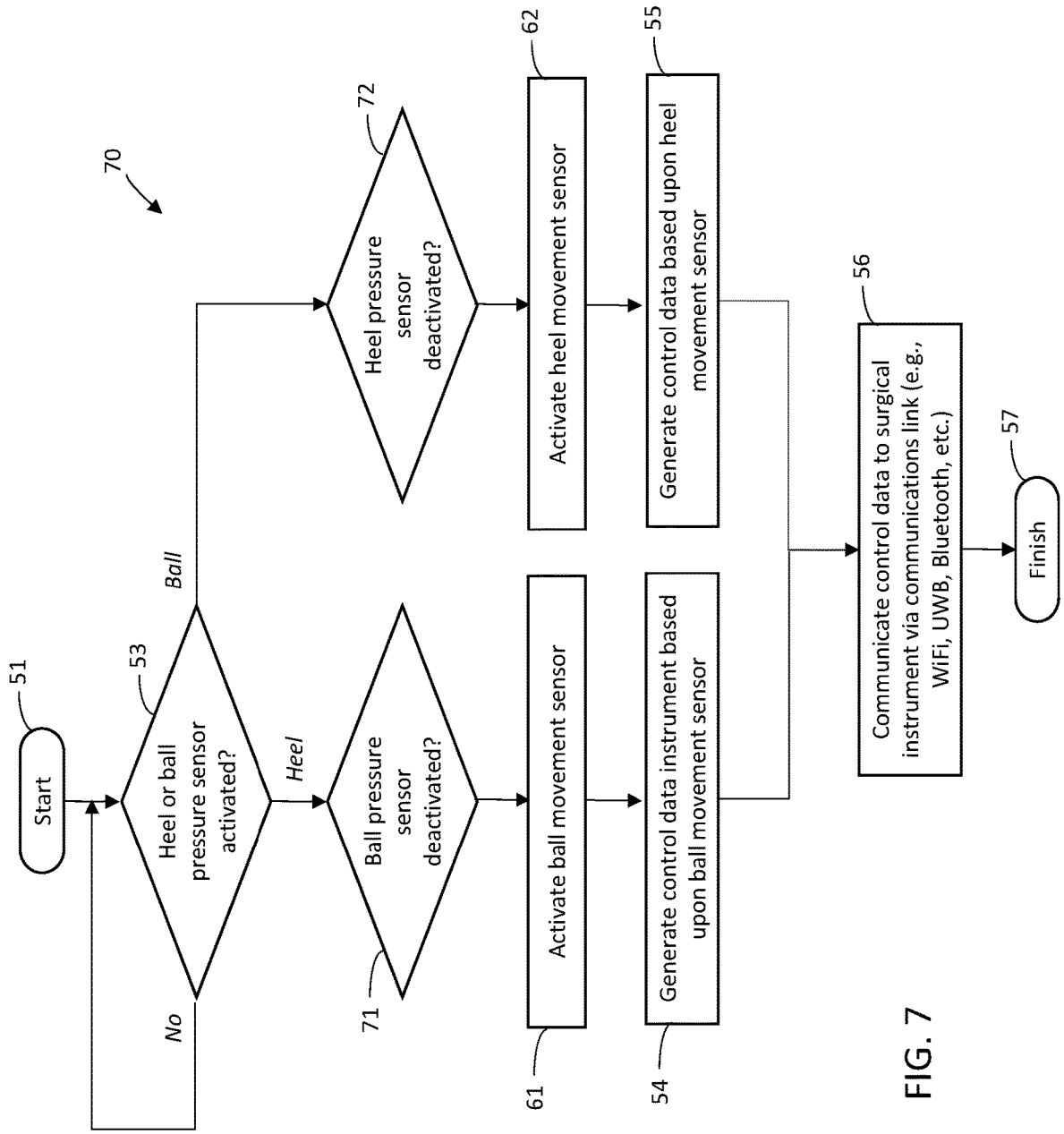

In the embodiment illustrated in FIGS. 6A and 6B, the processor 39 may further activate the ball movement sensor 38 responsive to activation of the heel pressure sensor 35 (Block 61), and activate the heel movement sensor 37 responsive to activation of the ball pressure sensor 36 (Block 62). This feature may be helpful for battery power savings, for example. Similarly, the heel and ball movement sensors 37, 38 may instead be activated responsive to deactivation of the heel and ball pressure sensors 35, 36, respectively (Blocks 71 and 72 of FIG. 7), which again may be beneficial for battery power savings, for example.

Furthermore, the processor 39 may be operable in a learning mode to associate one or more movements detected from the heel and/or ball movement sensors with a given control command, at Blocks 63-64. This may allow the user to define "macros" to perform a series of steps with less movements or at the same time, such as to zoom in a focus the microscope together. In some configurations, the processor 39 may be further configured to change a weight associated with the control data based upon an adjustable sensitivity ratio, at Blocks 65-66. More particularly, this may allow the user to adjust the granularity or sensitivity of movement he or she wishes to use to generate function commands for the surgical instrument 31 to personalize the user experience.

In some embodiments, the pressure sensors/touch pads 35, 36 alone (i.e., without a corresponding movement detected by the movement sensors 37, 38) may result in an output for controlling the medical instrument 31. More particularly, in some implementations certain foot positions/gestures may offer more reliable or consistent outputs when based upon the pressure sensors 35 or 36 as opposed to movement. For example, a "double tap" or "lift heel and tilt left and right on ball of foot" might be appropriate for pressure measurements alone versus gestures that are more appropriate for movement detection, like sliding a foot forward/backward/etc.

Many modifications and other embodiments will come to the mind of one skilled in the art having the benefit of the teachings presented in the foregoing descriptions and the associated drawings. Therefore, it is understood that the disclosure is not to be limited to the specific embodiments disclosed, and that modifications and embodiments are intended to be included within the scope of the appended claims.

The invention claimed is:
1. A wearable foot controller for a surgical instrument comprising:
a body configured to be worn on a foot and including a heel portion and a ball portion on an opposite end of the body from the heel portion;
a heel pressure sensor coupled to the heel portion of the body;

a ball pressure sensor coupled to the ball portion of the body;

a heel movement sensor coupled to the heel portion of the body;

a ball movement sensor coupled to the ball portion of the body; and a processor coupled to the body and configured to detect activation of the heel pressure sensor and generate control data for the surgical instrument based upon the ball movement sensor when the heel pressure sensor is activated, detect activation of the ball pressure sensor and generate control data for the surgical instrument based upon the heel movement sensor when the ball pressure sensor is activated, and communicate the control data to the surgical instrument via a communications link.

2. The wearable foot controller of claim 1 wherein the processor is further configured to activate the ball movement sensor responsive to activation of the heel pressure sensor, and activate the heel movement sensor responsive to activation of the ball pressure sensor.

3. The wearable foot controller of claim 1 wherein the processor is further configured to activate the ball movement sensor responsive to deactivation of the ball pressure sensor, and activate the heel movement sensor responsive to deactivation of the heel pressure sensor.

4. The wearable foot controller of claim 1 wherein the surgical instrument comprises a microscope; and wherein the control data relates to at least one of pan, tilt, zoom, illumination and focus of the microscope.

5. The wearable foot controller of claim 1 wherein the surgical instrument comprises a microscope; and wherein the control data relates to image recording using the microscope.

6. The wearable foot controller of claim 1 wherein the processor is operable in a learning mode to associate at least one movement detected from at least one of the heel and ball movement sensors with a given control command.

7. The wearable foot controller of claim 1 wherein the processor is further configured to change a weight associated with the control data based upon an adjustable sensitivity ratio.

8. The wearable foot controller of claim 1 wherein the processor is operable in an instructor mode in which the determined control commands override control commands from another surgical instrument controller.

9. The wearable foot controller of claim 1 wherein the processor is further configured to detect a series of movements from at least one of the heel and ball movement sensors, and switch between active and inactive states responsive to the series of movements.

10. The wearable foot controller of claim 1 wherein the communications link comprises a wireless communications link.

11. A method for controlling a surgical instrument using a wearable foot controller, the wearable foot controller comprising a body configured to be worn on a foot and including a heel portion and a ball portion on an opposite end of the body from the heel portion, a heel pressure sensor coupled to the heel portion of the body, a ball pressure sensor coupled to the ball portion of the body, a heel movement sensor coupled to the heel portion of the body, and a ball movement sensor coupled to the ball portion of the body, the method comprising:

detecting activation of the heel pressure sensor and generating control data for the surgical instrument based upon the ball movement sensor when the heel pressure sensor is activated;

detecting activation of the ball pressure sensor and generating control data for the surgical instrument based upon the heel movement sensor when the ball pressure sensor is activated; and communicating the control data from the wearable foot controller to the surgical instrument via a communications link.

12. The method of claim 11 further comprising activating the ball movement sensor responsive to activation of the heel pressure sensor, and activating the heel movement sensor responsive to activation of the ball pressure sensor.

13. The method of claim 11 further comprising activating the ball movement sensor responsive to deactivation of the ball pressure sensor, and activating the heel movement sensor responsive to deactivation of the heel pressure sensor.

14. The method of claim 11 wherein the surgical instrument comprises a microscope; and wherein the control data relates to at least one of pan, tilt, zoom, illumination and focus of the microscope.

15. The method of claim 11 wherein the surgical instrument comprises a microscope; and wherein the control data relates to image recording using the microscope.

* * * * *